United States Patent [19]

Knüttel

[11] Patent Number: 5,309,912
[45] Date of Patent: May 10, 1994

[54] MULTIDIMENSIONAL IMAGING USING A SINGLE POINT DETECTOR FOR A PHASE ENCODED MODULATED OPTICAL CARRIER

[75] Inventor: Alexander Knüttel, Kensington, Md.

[73] Assignee: The United States of America as represented by the Secretary of the Department of Health and Human Services, Washington, D.C.

[21] Appl. No.: 789,517

[22] Filed: Nov. 8, 1991

[51] Int. Cl.$^5$ .............................................. A61B 5/05
[52] U.S. Cl. .................................. 128/653.1; 128/665; 356/345
[58] Field of Search ...................... 128/653.1, 654, 655; 356/345, 349

[56] References Cited

U.S. PATENT DOCUMENTS

| | | |
|---|---|---|
| 3,273,458 | 9/1966 | Kohler . |
| 3,802,759 | 4/1974 | Anderson . |
| 4,118,106 | 10/1978 | Leith . |
| 4,592,361 | 6/1986 | Parker et al. ............... 128/664 |
| 4,786,124 | 11/1988 | Stone et al. . |
| 4,819,752 | 4/1989 | Zelin ......................... 128/664 |
| 4,906,092 | 3/1990 | O'Meara . |
| 5,088,493 | 2/1992 | Giannini et al. ............ 128/664 |
| 5,090,415 | 2/1992 | Yamashita et al. .......... 128/665 |
| 5,111,821 | 5/1992 | Potter ........................ 128/665 |

FOREIGN PATENT DOCUMENTS 590326 9/1985 Australia .
449337A2 6/1991 European Pat. Off. .

OTHER PUBLICATIONS

Fishkin et al., "Diffusion of Intensity Modulated Near-Infrared Light in Turbid Media", *Tissues*, SPIE, Los Angeles, Calif., Jan. 1991.
E. Gratton, et al., "A Continuously Variable Frequency Cross-Correlation Phase Fluorometer with Piscosecond Resolution", 44 *Biophys. J.*, 315-324, Dec. 1983.
Weng et al, "Measurement of Biological Tissue Metabolism Using Phase Modulation Spectroscopic Technology", SPIE vol. 1431, Time-Resolved Spectroscopy and Imaging of Tissues (1991) pp. 161-170.
Berndt et al, "Detection and Localization of Absorbers in Scattering Media Using Frequency-Domain Principles", SPIE vol. 1431, Time-Resolved Spectroscopy and Imaging of Tissues, 1991, pp. 149-159.

*Primary Examiner*—Lee S. Cohen
*Assistant Examiner*—Samuel Gilbert
*Attorney, Agent, or Firm*—Lowe, Price, LeBlanc & Becker

[57] ABSTRACT

Optical imaging of an object utilizes a plurality of amplitude modulated light rays propagating through the object, either sequentially or simultaneously, for detection by a single photodetector. The light rays may propagate geometrically (i.e., directly) or diffusively. Each of the rays is encoded with a different phase to provide sufficient information for decoding the light intensity detected by the photodetector. The rays may be applied simultaneously in an array, in which case different carrier frequencies as well as different phases are applied to the different rays by any of a number of modulators. Alternatively, the rays may be individually applied to the object in a sequence of phase encoded rays. In either case, the single photodetector receives sufficient information to image each of the voxels of interest in the object being imaged. Information may be obtained for different voxels selected for imaging without mechanical scanning.

17 Claims, 3 Drawing Sheets

MULTIDIMENSIONAL IMAGING USING A SINGLE POINT DETECTOR FOR A PHASE ENCODED MODULATED OPTICAL CARRIER

TECHNICAL FIELD

This invention relates to optical imaging, and more particularly to the use of phase encoding of an intensity modulated optical carrier in order to image a one-, two- or three-dimensional object using a single optical detector.

BACKGROUND ART

Numerous techniques and devices are known and available for imaging structures within opaque or turbid objects, such as biological tissue. Various examples of such prior art are provided in my copending U.S. application, Ser. No. 07/722,823, filed Jun. 28, 1991, the contents of which are hereby incorporated by reference.

The copending application describes a method and apparatus for imaging turbid media using optical interference among diffusively propagating, phase encoded, intensity modulated optical carriers, utilizing photons which pass through the medium (such as biological tissue) by the wave diffusion process as opposed to geometrically propagating "prompt" photons. As disclosed therein, a method for imaging an object includes the steps of applying modulated optical rays at a plurality of points along a surface of the object, each of the rays characterized by an amplitude modulated at a respective modulating frequency and by a specific phase. The phases applied to the various rays are provided respective relative phase-shifts which are selected to cause constructive interference among the modulated rays at a predetermined volume element of interest, or voxel.

Thus, the method effectively selects the predetermined voxel for imaging by selecting the relative phase-shifts to be applied to the intensity modulated light rays. In accordance with the method, the modulated rays are diffusively propagated through the object and the intensity and phase of a light ray resulting from the constructive interference at the selected voxel are detected in order to image a characteristic of the voxel.

In order to image a portion of the object which includes a number of voxels, the method of the copending application may include the further steps of repeating the selecting step for a sequence of predetermined voxels, repeating the propagating step to diffusively propagate the modulated rays through the object to the predetermined voxels, and repeating the detecting step to detect rays respectively resulting from a sequence of constructive interferences at the sequence of voxels. For such a process, the selecting step preferably includes the steps of using a signal responsive phase shifting device, such as a zone plate, for applying the relative phase-shifts to the rays. Computer generated signals are applied to the signal responsive phase shift device, thereby providing non-mechanical scanning of the portion of the object to be imaged.

Although the above summarized invention disclosed in my copending application solves a number of problems associated with the prior art, the disclosed method and apparatus provides for imaging of absorption characteristics using interference among diffusively propagating modulated light rays. There accordingly remains a need for method and apparatus capable of imaging attenuation and phase delay characteristics of an object, using a simplified detector structure and not necessarily relying on occurrence of an optical interference at the object.

In that regard, the prior art uses an optical mask which is time encoded to permit various light rays to impinge on specific voxels of an object. After passing through the object, the rays emerge with intensity attenuation and phase change determined by the characteristics of the voxels. The emergent rays are directed to be incident on corresponding photodetectors for imaging thereby. Such a prior art arrangement is illustrated in FIG. 8, wherein a n plurality of intensity modulated light rays $r_i$ are transmitted through corresponding voxels $V_i$ ($i=1, 2, 3, \ldots, 4$) of an object 10 for detection by a photodetector array 13. A mask 11 includes a plurality of opaque and transparent regions in the paths of light rays $r_i$ to transmit or block specific rays to the object and to establish a specific timing sequence of rays for incidence on the object.

Such a mask may be a computer controlled liquid crystal plate, for example, having pixels or pixel groups which are selectively made opaque and transparent according to a predetermined timing sequence. In the Figure there is illustrated a single transparent region 15 in mask 11, the remaining regions being opaque. By having a predetermined time sequencing for the incident rays as well as for reading and processing of outputs of the photo-detectors 13, a processor 16 obtains a distribution of the intensity (amplitude) attenuation and phase shifting characteristics of the various voxels of the object, thus imaging the object.

However, such a prior art approach as shown in FIG. 8 requires a complex sequencing arrangement of the imaging rays, requires a complex photodetecting structure utilizing a number of photo-detectors, and requires passage of time from the application of the first imaging ray to the last such ray, thus effectively prohibiting the system from obtaining a real-time "snapshot" of the voxels of the object.

There is thus a need in the prior art for method and apparatus of using a single detector cell rather than an array of cells for imaging attenuation and phase delay characteristics of one or more elements which are arrayed along a plurality of dimensions of an object, whether the imaging uses a single exposure or a plurality of exposures.

There is yet a more particular need for a method and apparatus for imaging a plurality of voxels of an object of interest, whether disposed as a one-dimensional linear array, as a two-dimensional planar array, or as a three-dimensional volume of the object, by a single exposure of the array of voxels to imaging light including a plurality of phase-encoded, modulated optical carrier frequencies.

There is yet another need in the prior art for imaging one or more voxels of an object by applying one or more rays of light to the voxels, in one or more exposures, using geometrically propagating light rays.

DISCLOSURE OF INVENTION

It is accordingly an object of the present invention to provide a method and apparatus for imaging attenuation and phase delay characteristics of an object requiring a simplified detector structure and without requiring optical interference to occur at the object.

It is a more specific object to provide a method and apparatus for imaging attenuation and phase delay characteristics of multiple dimensions of an object using a single detector cell rather than an array of cells, whether by a single exposure of a plurality of rays or by a plurality of sequential exposures, each to a single ray.

It is a more particular object of the invention to provide a method and apparatus for imaging a plurality of voxels of an object of interest, whether disposed as a one-dimensional, linear array, as a two-dimensional, planar array, or as a three-dimensional volume of the object, by exposing the voxels in a single exposure to imaging light including a plurality of phase-encoded, intensity modulated optical carrier frequencies.

Another object is to image one or more voxels of an object by applying one or more rays of light to the voxels, in one or more exposures, using geometrically and/or diffusively propagating light rays.

It is still a more specific object of the invention to provide method and apparatus for obtaining optical attenuation and phase delay data descriptive of optical characteristics of an object, thereby to image an object, free of requirements for exposure of the object to ionizing radiation and free of a requirement for administration of contrast or tracing agents.

Still another object of the invention is to provide method and apparatus utilizing a single detector for obtaining substantially simultaneously imaging data descriptive of optical characteristics of an entire volume of an object, thus simultaneously imaging the entire object.

In accordance with these and other objects of the invention, there is provided an improvement in an apparatus for imaging attenuation and phase shift characteristics of an object including applying means for applying to a surface of the object a plurality of electromagnetic rays, each having a carrier frequency in an optical frequency spectrum, each of the rays modulated by a modulation frequency, and detecting means for detecting the electromagnetic rays after attenuation and phase shifting by each of a plurality of voxels (volume elements of interest). In accordance with the invention, the imaged voxels are disposed in an array of n dimensions where n is at least equal to 1, thus providing for imaging of a single voxel, a linear array, a 2-dimensional array, and a volume array of voxels. Moreover, the detecting means includes only a single optical detecting cell for detecting electromagnetic radiation resulting at a single point from attenuation and phase shift of the rays by the plurality of voxels. Moreover, the invention includes a processor for processing an output signal from the single cell to provide data identifying optical attenuation and phase shift characteristics of each of the voxels thereby to image the plurality of voxels.

The invention moreover provides for the amplitude modulated rays to be applied either in a sequence of individual rays or simultaneously, as an array of differently modulated rays. Of course, the detecting means could be reflective or transmissive.

In an embodiment providing for simultaneous application of the rays to the object in an array of modulated rays, the improved imaging apparatus preferably further includes a phase array means for providing a predetermined phase shift to each of the electromagnetic rays in the array, thereby to phase encode the electromagnetic rays incident on the surface of the object. The phase array means may include a plurality of optical paths having various different path lengths, thus providing various different phase shifts to the rays.

Thus, the phase array means may include a plurality of free space optical paths each including means for receiving a respective ray and means establishing a predetermined free space optical path for the respective ray. Moreover, the means establishing may include a corner cube reflector displaced by a predetermined distance from the means for receiving, thereby providing a predetermined optical path and a predetermined phase shift to a ray prior to incidence of the ray on a respective voxel to be imaged thereby.

Alternatively, the phase array means may include a plurality of fiber optical paths, wherein each optical path includes means for receiving a respective ray and a predetermined length of optical fiber between the means for receiving and the surface of the object, in order to provide a predetermined optical path and a predetermined phase shift to a ray prior to incidence of the ray on a respective voxel to be imaged thereby.

Additionally, the improved imaging apparatus may provide (in the phase array means) a plurality of condition responsive optical devices for modulating each of the electromagnetic rays and for providing predetermined phase shifts to each of the rays modulated thereby.

Therein, the condition responsive optical devices may include a plurality of electro-optic means. Each of these means receives an unmodulated electromagnetic ray and is connected to receive an electrical signal from a source of electrical signals to modulate the ray received thereby at a predetermined frequency and phase in order to provide the predetermined phase shifts to each of the rays.

Alternatively, the condition responsive optical devices may include a plurality of acousto-optic means each receiving an unmodulated electromagnetic ray and connected to receive an acoustic signal to modulate the ray received thereby at a predetermined frequency and phase, in order to provide the predetermined phase shifts to each of the rays.

As yet another alternative, the condition responsive optical devices may include a plurality of opto-optic means each receiving an unmodulated electromagnetic ray and connected to receive an optical signal, thus to modulate the intensity of the ray received thereby at a predetermined frequency and phase in order to provide the predetermined phase shifts to each of the rays.

In its generic form, the applying means of the invention includes modulating means for modulating each of the plurality of electromagnetic rays by a respective modulation frequency, thereby producing a plurality of electromagnetic rays modulated at respective modulation frequencies, for application to the surface of the object.

In an embodiment providing for simultaneous application of the rays to the object the applying means may further include phase array means for providing a respective predetermined phase shift to each of the modulated electromagnetic rays thereby to phase encode the electromagnetic rays incident on the surface of the object. Thus, the phase shifting is applied to the amplitude modulated rays.

The modulating means of this embodiment preferably operates to amplitude modulate the beam intensity of each electromagnetic ray by a modulation frequency less than approximately one percent of the carrier frequency.

Moreover, the modulating means may include means for amplitude modulating the beam intensity of each of the electromagnetic rays by a different modulation frequency.

In accordance with another aspect of the invention, the differently phase encoded rays may be applied to the object sequentially, rather than simultaneously. In this embodiment, the applying means includes sequencing means for sequentially applying the plurality of electromagnetic rays to the object.

Thus, the invention also encompasses an apparatus for imaging attenuation and phase shift characteristics of an object including applying means for sequentially applying to a surface of the object a sequence of intensity modulated electromagnetic rays each having a carrier frequency in an optical frequency spectrum, and after attenuation and phase shifting by each of a plurality of voxels. The detecting means includes only a single optical detecting cell for detecting electromagnetic radiation resulting at a single point from attenuation and phase shift of each of the sequentially applied rays by the plurality of voxels. A processing means processes an output signal from the single cell to provide data identifying optical attenuation and phase shift characteristics of each of the voxel. The applying means includes modulating means for modulating each of the electromagnetic rays, thereby producing a sequence of intensity modulated electromagnetic rays, and for sequentially applying the modulated electromagnetic rays to the surface of said object.

With respect to the broad aspects of the invention, a single detector may be used to image, or provide characteristics descriptive of, a single voxel of the object by using a single detector cell for detecting intensity and phase of a light ray passing through or reflected by the selected voxel, the cell thus imaging the voxel as a function of the intensity and phase of the detected light ray.

Further, the optical rays are modulated as part of the inventive method. Particularly, where a signal responsive device is used to modulate the intensity of the optical rays, the signal responsive device may also be used to provide the selected phase shifts to the various beams.

Thus, the object being imaged may be imaged by a single detector cell receiving a plurality of separately phased rays. Where the rays are applied simultaneously the image provides an snap-shot of the portion of interest in the object Where the rays are applied in a timed set the single photodetector effectively provides a non-mechanical scan of the array of voxels. The intensity and phase information of the detected rays provide solutions to a plurality of equations describing relationships between the detected information and the transmitted rays, the solution providing a distribution of the attenuation and phase delay characteristics of the object (i.e., providing an image of the object).

BRIEF DESCRIPTION OF THE DRAWINGS

The accompanying drawings, incorporated into and forming a part of the specification, illustrate several aspects of a preferred embodiment of the present invention and, together with the description, serve to explain the principles of the invention. In the drawings.

BEST MODE FOR CARRYING OUT THE INVENTION

Figure 1:
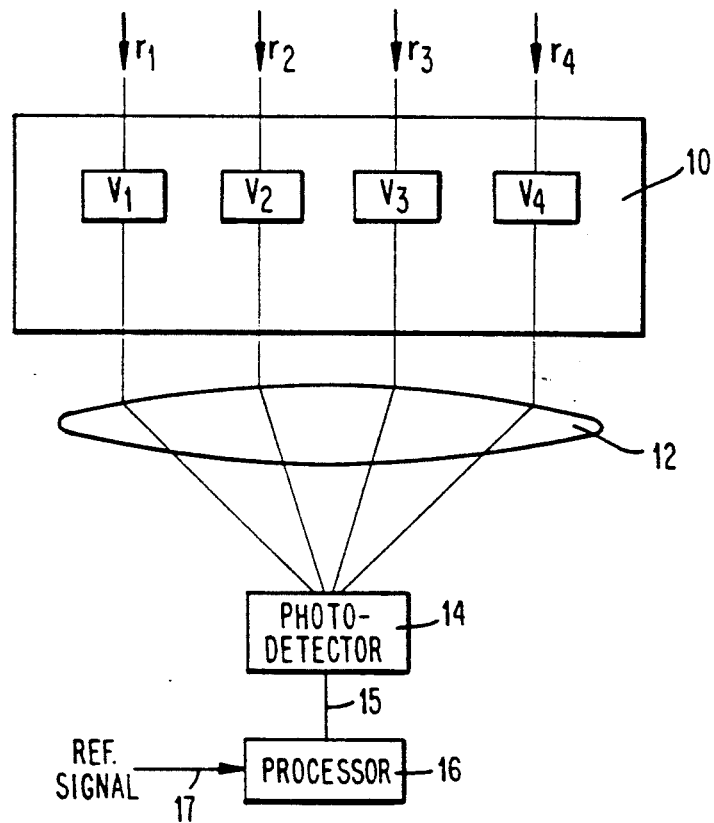
FIG. 1 illustrates a preferred embodiment of the present invention.

Referring now to the drawings, there is shown in FIG. 1 an embodiment of the broad concepts of the present invention.

Prior to describing the embodiment illustrated therein, however, it should be noted that the term optical imaging of an object as used herein relates to detection of a light ray transmitted through, or reflected by, the object of interest and specifically transmitted through or reflected by various internal components of the object. Hereinafter, reference to a light ray received from (or transmitted through) such an element should be understood to include both transmitted and reflected rays, as explained below with respect to possible modifications of FIG. 1.

The detected light ray contains information descriptive of various characteristics of the object or its internal components. For example, the information may be descriptive of the absorption characteristics of the internal structural components of the object, or may be descriptive of density, fluorescence, or other characteristics thereof. The present invention is directed at apparatus for detecting specific imaging characteristics of the internal structure of an object, and specifically at detection of the characteristics of a specific portion of an object which affect intensity attenuation and phase delay characteristics of light rays passing therethrough or reflected thereby, and thus at an ability to provide an optical image of a desired portion of an object of interest, whether the desired portion is at the surface of the object or deep within the object.

Further, use of the term "optical" or "light" rays generally refers to electromagnetic radiation, in the visible frequency range of approximately $4 \times 10^{14} - 8 \times 10^{14}$ Hz with wave lengths in the range of approximately 0.75 to 0.38 micron. However, the present invention is not necessarily limited to the visible spectrum of electromagnetic radiation and other spectra of the electromagnetic continuum may be utilized, to the extent practicable.

As hereinabove noted, FIG. 1 provides a schematic illustration of an embodiment of the present invention, wherein, similarly to the prior art, a plurality of intensity modulated light rays $r_i$ are transmitted through corresponding voxels $V_i$ (i = 1, 2, 3, ..., 4) of an object 10 for detection by a detector 14 and for subsequent imaging.

In that regard, detecting device 14 may be any type of light sensitive device, whether a vacuum type photomultiplier tube (PMT), a solid state device, or the like. Photodetector 14 converts the optical radiation incident thereon to electrical signals in a known manner. The resultant electrical signals are then processed in a well known manner, to obtain numerical data or to generate displays as hereinabove summarized. Moreover, although photodetector 14 is shown as receiving the light transmitted through object 10, and is thus on an opposite side of the object from the incident light rays, it is also known to provide the photodetector 14 on the same side of the object 10 as the incident light rays, in which case reflected light rays are processed for imaging. Thus, imaging may utilize light rays transmitted through or reflected by the object, and specifically by internal voxels $V_i$ within the object being imaged, in order to provide information descriptive of the internal structure of the object.

It should also be recognized that the one dimensional array of voxels illustrated in FIG. 1 is merely illustrative of the manner in which the voxels of interest may be distributed in the object. That is, the portion of the object which is of interest for imaging may be a linear portion, as represented by the illustrative linear array of voxels. Alternatively, however, the portion of interest may be a surface, represented by a two-dimensional array of voxels, or a volume, represented by a three-dimensional array. Thus, any arbitrarily shaped portion of the object may be imaged using the concepts of the present invention as described herein.

In accordance with the invention, the light rays passing through and emerging from object 10 are focused by a lens 12 on a single photodetector 14, which generates an output signal 15 representative of the detected illumination.

The output signal 15 represents the intensity of the optical illumination incident on the photodetector 14 and thus provides a specific time waveform to processor 16 for analysis. The amplitude of the signal provided to the processor 16 represents the results of attenuation of the original light rays $r_i$ by the voxels $V_i$, while the timing of the signal represents phase shifts imparted to the incident rays by the voxels. Such phase shifts represent information descriptive of the absorption coefficients, scattering coefficients, and fluorescence decay of the voxels $V_i$. Accordingly, a reference signal 17 is provided to the processor representative of the phase of the incident rays $r_i$, for use in conjunction with the signal 15 to determine the phase shifts imparted thereto by the voxels being imaged.

The light rays $r_i$ are each a modulated light ray, having a specific carrier frequency (e.g., $\omega_o$) provided with an amplitude modulation of a given frequency ($\omega_j$). Each voxel, depending on its specific composition and other physical characteristics, will have a particular attenuation coefficient ($A_i$) and phase delay ($\Delta\omega_j$). characteristic for the frequency $\omega_o$. Upon determining the characteristics $A_i$ and $\Delta\omega_i$ of each of the voxels forming the portion of interest, an image of the portion of interest can be generated by plotting the characteristics, whether on a CRT, LCD, or other display or by printing or generating other hard copy outputs representative thereof.

Upon applying to the $i^{th}$ voxel of the object a $j^{th}$ incident ray, with modulation frequency $\omega_j$, but without the phase shift of the present invention, the attenuation and phase delay exerted by the voxel will result in an exiting ray incident on photodetector 14 having an intensity $\psi_j$ given by Equation (1):

$$\psi_j(A,\Delta\phi) = \sum_{i=1}^{k} A_i \sin(\omega_j t + \Delta\phi_i) \quad (1)$$

This equation reflects the intensity of the $j^{th}$ exiting ray as being a summation of the illumination passing through each of the voxels (summation over the index i) after attenuation by the attenuation coefficient thereof and delay by the phase delay characteristic. Standard mathematical calculations (such as a Gaussian elimination procedure described by Bronstein) may be used to obtain a plurality of equations in order to solve for the plural coefficients $A_i$ and $\Delta\phi_i$.

If the individual rays are individually applied, so that the individual output signals 15 can be associated with individual rays, the above equations may be solved. That is, by knowing which beam is being applied at a particular time and which voxel is primarily responsible for the ray impinging on the photodetecting array, it is possible to obtain information on the attenuation coefficient and phase delay characteristic of that voxel. Individual application of the rays, however, requires a sequential application of light rays, and/or utilization of a plurality of detectors to obtain a plurality of output signals. It is impossible to solve the plurality of equations resulting from simultaneous application of a plurality of rays together with simultaneous detection of the exiting rays from a plurality of voxels by a single detector, because the equations become redundant.

In accordance with the invention, and to enable simultaneous application of a plurality of rays and simultaneous detection thereof by a single detector, the above noted redundancy of equations is eliminated by phase encoding each of the incident rays. That is, to each incident ray there is provided not only a modulating frequency $\omega_j$, but also a specific relative phase angle $\phi_{ij}$.

The term $\phi_{ij}$ contains the phase information of the $j^{th}$ ray before impinging on the $i^{th}$ voxel, which may include effects of the different path length from the source to the various voxels. Thus, rather than Equation (1), the phase encoding provided by the present invention results in a set of equations of the type in Equation (2):

$$\psi_j(A,\Delta\phi) = \sum_{i=1}^{k} A_i \sin(\omega_j t + \phi_{ij} + \Delta\phi_i) \quad (2)$$

The added phase encoding term $\phi_{ij}$ eliminates the redundancy and enables solution of the k vector equations in 2k unknowns ($A_i$ and $\Delta\phi_i$ for i=1, 2, ... ,k) to obtain real and imaginary components of the detected intensity, as shown in Equations (3) and (4), respectively:

$$\psi_{jR} = \left[\sum_i A_i \sin(\phi_{ij} + \Delta\phi_i)\right] \cos\omega_j t \quad (3)$$

and $$\psi_{jI} = \left[\sum_i A_i \cos(\phi_{ij} + \Delta\phi_i)\right] \sin\omega_j t \quad (4)$$

The above thus results in at least 2k equations in 2k unknowns, describing detected intensity for a plurality of geometrically propagating light rays passing through a number of voxels. Upon slight modification, the equations are substantially equally applicable for diffusively propagating light rays. The plurality of equations may be solved by application of the known Gaussian elimination procedure to obtain values for the attenuation coefficients $A_i$ and the phase delay characteristics $\Delta\phi_i$ of each of the voxels of interest. Thus, the present invention permits imaging of a portion of an object by simultaneous application of a plurality of intensity modulated phase encoded light rays, obtaining a real-time "snapshot", or by obtaining a non-mechanical scan of the object by application of a sequence of rays thereto. In either case, only a single photodetector is required, though an array including a plurality of detectors may be used.

It should be noted that the modulation frequencies $\omega_j$ are related to the carrier frequency of the light ray by the relationship $$\omega_j << \omega_c.$$

Thus, by using a central modulating frequency of approximately 1 GHz, which is approximately $2\times10^{-6}$ (0.0002%) of the frequency of light, it is assured that even with uses of 100 different modulation frequencies $\omega_j$ at 100 kHz spacing, or a bandwidth of approximately $\pm 10$ MHz from the central modulating frequency, the attenuation coefficients and phase delay characteristics of the voxels are relatively constant for each of the incident phase-encoded rays.

An advantage of utilizing a modulating frequency on the order of GHz is that very large wavelengths are involved, thus enabling measurement of the very small phase delays associated with the voxels being imaged. The bandwidth of modulating frequencies is deliberately kept small to avoid errors arising from dependence of $\Delta\phi_i$ on frequency in some media. Thus, preferably the bandwidth is kept less than $\pm 1\%$, as by limiting the bandwidth to $\pm 10$ MHz for a central modulating frequency of approximately 1 GHz.

Use of different modulating frequencies permits simultaneous collection of all exiting light rays to enable the above noted parallel, rather than sequential, solution of equations (3) and (4) and the resultant equivalent of "flash", or "snap-shot", imaging of the object.

The following description provides details of several alternative embodiments for generating the plural phase-encoded rays used in conjunction with the invention.

Figure 2:
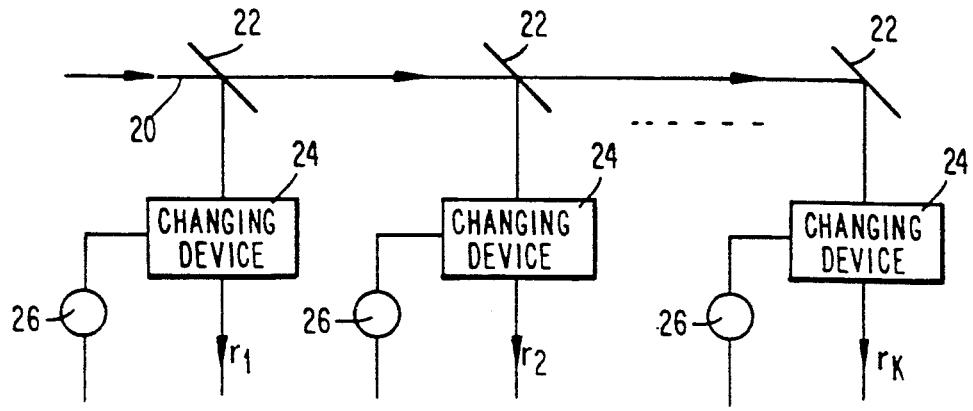
FIG. 2 is an illustration of a generic structure used in implementing the embodiment of FIG. 1.

Referring now to FIG. 2, there is shown a general illustration of a structure for providing the plurality of phase-encoded light rays $r_1, r_2, \ldots, r_k$ for imaging the object of interest. A light source (not shown), which is typically a laser, generates a light ray 20 to be directed at object 10. A plurality of beam splitters 22 direct portions of he unmodulated light ray 20 at a plurality of controlled phase changing devices 24. Control circuits 26 are used to control the devices 24 to provide the desired phase angles to the rays passing therethrough, thus to result in the incident rays $r_1, \ldots, r_k$.

Thus, the illustrated structure includes an array of devices which effectively provides a phased array of modulated coherent light rays. The devices 24 used in FIG. 2 may be an array of electro-optic, acousto-optic, or opto-optic devices, for example, which are driven by sinusoidal signals of predetermined phase relationships provided by appropriate control circuits 26. The devices 24, which provide phase modulation to the portions of incoming light ray 20, may thus also be used to provide the specific intensity modulation thereto. Thus, the embodiment of FIG. 2 effectively utilizes optical modulators, which receive input control signals oscillating at the modulation frequency at the predetermined phase distribution to be applied to the light rays. This embodiment provides for both modulation and phase encoding of the coherent light rays.

Figure 3:
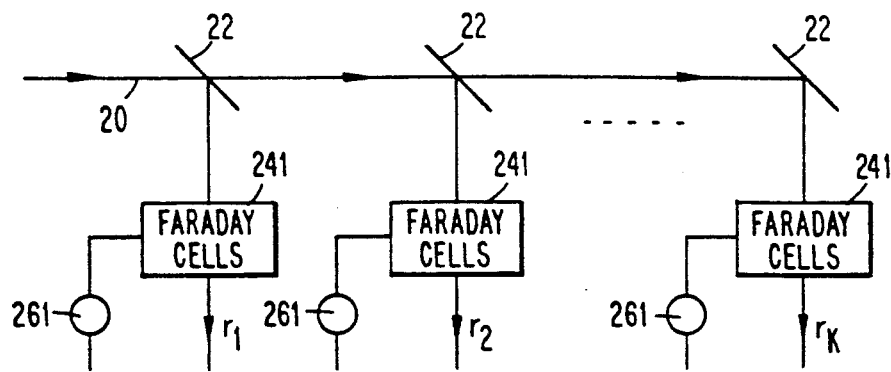
FIG. 3 shows a first specific embodiment of the structure of FIG. 2.

In one form, the controlled phase changing devices 24 may be electro-optic devices, such as faraday cells 241 illustrated in FIG. 3. In this embodiment, each cell is driven by the corresponding control circuit 261 at a respective frequency $\omega_j$ and at a relative phase angle $\phi_{ij}$.

Figure 4:
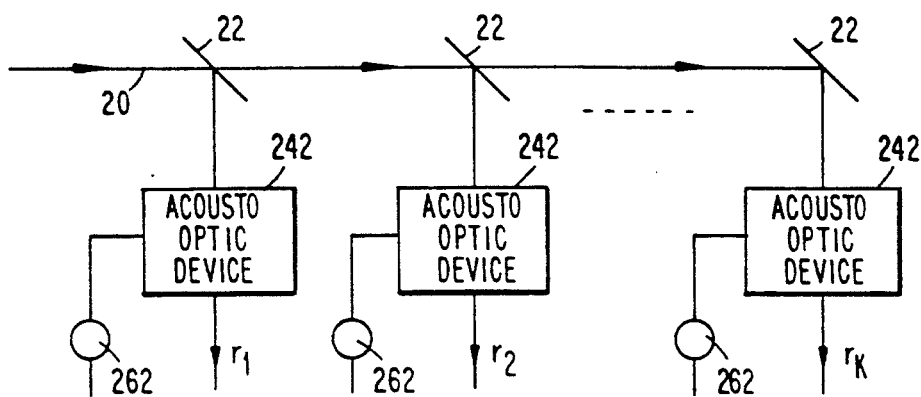
FIG. 4 shows a second specific embodiment of the structure of FIG. 2.

In another form, the controlled phase changing devices 24 may be acousto optic devices, illustrated at 242 in FIG. 4, wherein each device is driven by a corresponding control circuit 262 at the respective frequency and relative phase angle.

Figure 5:
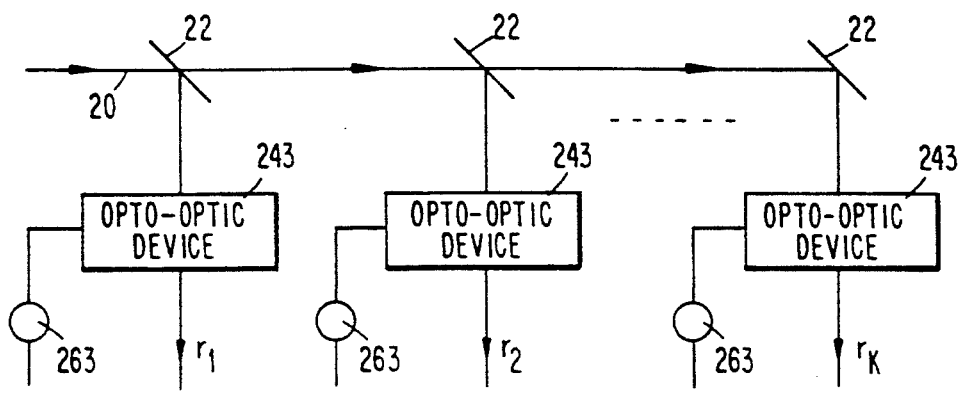
FIG. 5 shows a third specific embodiment of the structure of FIG. 2.

As yet another embodiment of the structure of FIG. 2, the controlled phase changing devices 24 may be an array of opto-optic devices (e.g., SEED's, self electro-optical devices) for providing the properly phased array of modulated light rays. Such devices, similarly to the above described modulators, are also capable of modulating the light rays in a known manner. This embodiment, which is particularly useful for miniaturization and for improved resolution, is illustrated in FIG. 5. As shown therein, an array of opto-optic devices is arranged so that each device is driven by a corresponding control circuit 263.

Still another modification of the invention (not shown) utilizes computer driven pixels of a LCD plate to provide the appropriate phasing and modulation for the incoming laser beam 20.

In yet another embodiment, the invention contemplates the use of free space and optical fibers as means for varying the path length travelled by the rays provided by a plurality of beam splitters. Thus, as shown in FIG. 6, a free-space phase encoding structure may be used to implement the concept of the invention as follows.

A modulated light beam 30 is split by a series of beam splitters 22. In this embodiment, the light beam is already modulated, and the structure of FIG. 6 is used only to provide the appropriate phase encoding of the incident light rays $r_1, \ldots, r_k$ as hereinabove described. Towards that end, there is provided a plurality of corner cube (or similar) reflectors 32 to assure that the portions of light beam 30 obtained by beam splitters 22 are redirected to the object 10.

The respective reflectors 32 are each spaced from the object by a respective path length 34, 34' and 34", for example, thus to provide a different path length, and a correspondingly different phase angle, for each ray incident on the object. As will be appreciated by those of ordinary skill, the embodiment of FIG. 6 utilizes free space as an optical delay line, wherein path lengths are selected in a known manner to provide the appropriate phase angle in accordance with the frequency of the light ray.

Figure 6:
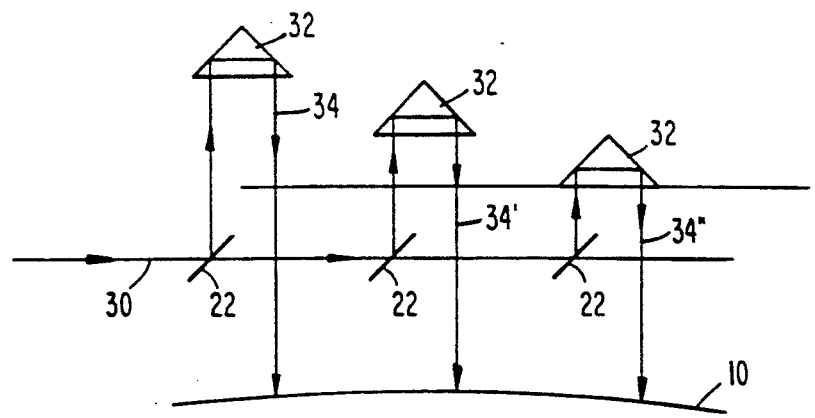
FIG. 6 shows a free-space phase encoding structure used in implementing the embodiment of FIG. 1.
Figure 7:
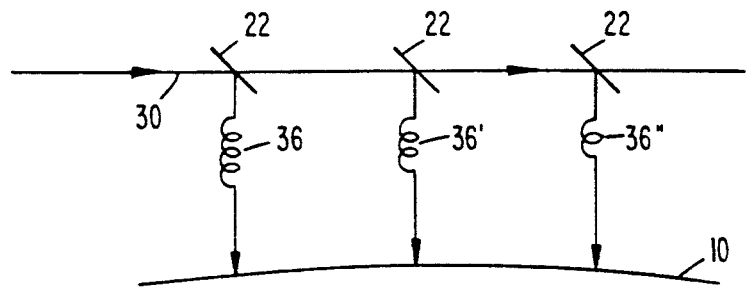
FIG. 7 shows an optical fiber phase encoding structure used in implementing the embodiment of FIG. 1.
Figure 8:
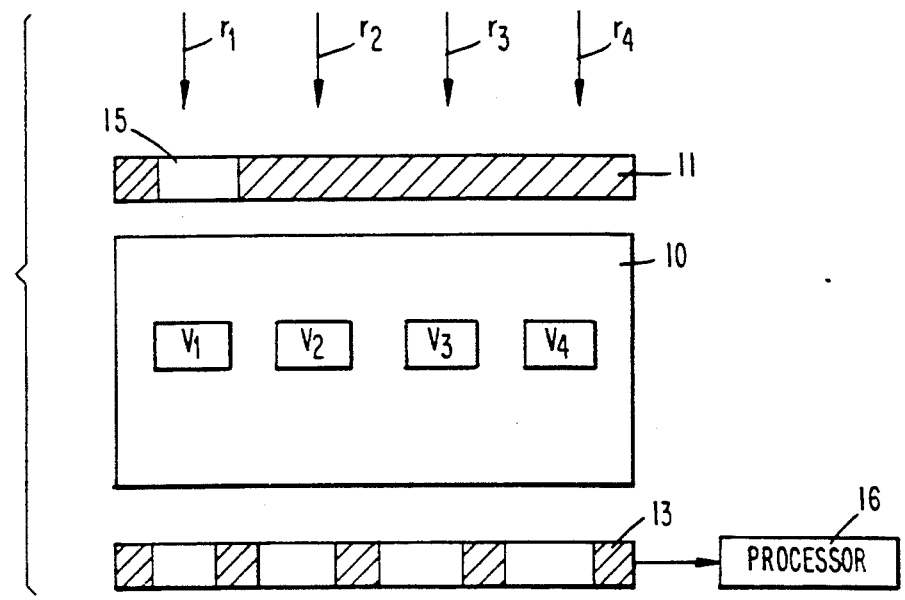
FIG. 8 shows a prior art arrangement for imaging an object.

FIG. 7 shows another embodiment utilizing the principle contemplated in the embodiment of FIG. 6. However, rather than utilizing an array of reflectors, the embodiment of FIG. 7 utilizes optical fibers, or other light transmitting or conducting devices, to provide the various different path lengths to the respective light rays, and thus to provide the respective phases thereto. As shown in the Figure, an array of beam splitters 22 is used to obtain the various light rays from the incoming modulated light beam 30. Each light ray is transmitted through a respective optical fiber 36, 36', ..., 36" of predetermined length, thus to provide the desired predetermined relative phase displacement thereto.

As will be appreciated, the embodiment of FIG. 7 utilizes bundles of optical fibers of different lengths which form a plurality of delay lines. By passing the coherently modulated light rays through the fibers the proper phasing is provided to a plurality of light rays incident on the object to be imaged.

In the embodiments of FIGS. 6 and 7, a single modulator is used to output a modulated light beam to one of several fibers (or free-space paths) of different lengths in order to provide a desired amplitude and phase modulation. Where it is desired to use sequential application of the light rays, optical switching may be used to switch the different length fibers (or free-space paths) to the modulator to provide the different phase angles to the rays.

Although a single light beam 30 is shown in the embodiments of FIGS. 6 and 7, it should be appreciated that a plurality of beams, modulated at respective frequencies, may be used. Alternatively, the light source used to provide the light beam may be a mode locked laser which produces a frequency comb of modulation frequencies.

In accordance with the invention, there has thus been provided a method and apparatus for imaging of an object by simultaneous or sequential application of a plurality of intensity modulated light rays. The light rays are phase encoded, and imaging may be simultaneously achieved with a single detecting cell when different modulating frequencies are applied. Where the differently phased rays are sequentially applied to the object and imaged by the single detecting cell in a sequence, there effectively results a non-mechanical scanning of an arbitrarily selected array of voxels within the object. Where the different phases are provided in superposition there results simultaneous acquisition and imaging of data for the selected array of voxels by a single detecting cell. Light rays of different modulation frequencies may be used to provide simultaneous imaging by a single cell.

The foregoing description of the preferred embodiments of the invention has been presented for purposes of illustration and description. It is not intended to be exhaustive or to limit the invention to the precise forms disclosed since many modifications or variations thereof are possible in light of the above teaching. All such modifications are within the scope of the invention. The embodiments described herein were chosen and described in order best to explain the principles of the invention and its practical application, thereby to enable one of ordinary skill in the art to utilize the invention in various embodiments and with various modifications as are suited to the particular use contemplated therefor. It is intended that the scope of the invention be defined by the claims appended hereto, when interpreted in accordance with full breadth to which they are legally and equitably entitled.

I claim:

1. In an apparatus for imaging attenuation and phase shift characteristics of an object including applying means for applying to a surface of the object a plurality of electromagnetic rays each having a carrier frequency in an optical frequency spectrum, each of said rays modulated by a modulation frequency, and detecting means for detecting the electromagnetic rays after attenuation and phase shifting by each of a plurality of voxels (volume elements of interest), the improvement wherein said voxels are disposed in an array of n dimensions where n is at least equal to 1 and said detecting means comprises only a single optical detecting cell for detecting electromagnetic radiation resulting at a single point from attenuation and phase shift of said plurality of rays by said plurality of voxels, and processing means for processing an output signal from said single cell to provide data identifying optical attenuation and phase shift characteristics of each of said voxels thereby to image said plurality of voxels.

2. An improved imaging apparatus in accordance with claim 1 wherein said electromagnetic rays are applied to the object substantially simultaneously in an array of a plurality of rays, and further comprising phase array means for providing a predetermined phase shift to each of said electromagnetic rays thereby to phase encode the electromagnetic rays incident on the surface of the object.

3. An improved imaging apparatus in accordance with claim 2 wherein said phase array means comprise a plurality of optical paths having various different path lengths, thus providing various different phase shifts to said rays.

4. An improved imaging apparatus in accordance with claim 3, wherein said phase array means comprises a plurality of free space optical paths each including means for receiving a respective rays and means establishing a predetermined free space optical path for the respective ray, said means establishing including a corner cube reflector displaced by a predetermined distance from said means for receiving thereby providing a predetermined optical path and a predetermined phase shift to the respective ray prior to incidence of the respective ray on a respective voxel to be imaged thereby.

5. An improved imaging apparatus in accordance with claim 3, wherein said phase array means comprises a plurality of fiber optical paths each optical path including means for receiving a respective ray and a predetermined length of optical fiber between said means for receiving and said surface of said object thereby providing a predetermined optical path and a predetermined phase shift to the respective ray prior to incidence of that ray on a respective voxel to be imaged thereby.

6. An improved imaging apparatus in accordance with claim 2 wherein said phase array means comprises a plurality of condition responsive optical devices for modulating each of said electromagnetic rays and for providing predetermined phase shifts to each of said rays modulated thereby.

7. An improved imaging apparatus in accordance with claim 6 wherein said condition responsive optical devices comprise a plurality of electro-optic means each receiving an unmodulated electromagnetic ray and connected to receive an electrical signal from a source of electrical signals to modulate the ray received thereby at a predetermined frequency and phase to provide said predetermined phase shifts to each of said rays.

8. An improved imaging apparatus in accordance with claim 6 wherein said condition responsive optical devices comprise a plurality of acousto-optic means each receiving an unmodulated electromagnetic ray and connected to receive an electromagnetic signal which is transformed thereby to an acoustic signal to modulate the received ray at a predetermined frequency and phase to provide said predetermined phase shifts to each of said rays.

9. An improved imaging apparatus in accordance with claim 6, wherein said condition responsive optical devices comprise a plurality of opto-optic means each receiving an unmodulated electromagnetic ray and connected to receive an optical signal to modulate an intensity of the ray received thereby at a predetermined frequency and phase to provide said predetermined phase shifts to each of said rays.

10. An improved imaging apparatus in accordance with claim 1, wherein said applying means comprises modulating means for modulating each of said plurality of electromagnetic rays by a respective modulation frequency thereby producing a plurality of electromagnetic rays modulated at respective modulation frequencies, and for applying said plurality of modulated electromagnetic rays to said surface of said object.

11. An improved imaging apparatus in accordance with claim 10, wherein said plurality of electromagnetic rays are applied to the object substantially simultaneously in an array, and wherein said applying means further comprise phase array means for providing a respective predetermined phase shift to each of said modulated electromagnetic rays thereby to phase encode the electromagnetic rays incident on the surface of the object.

12. An improved imaging apparatus in accordance with claim 11 wherein said phase array means comprises a plurality of optical paths having various different path lengths, thus providing various different phase shifts to said rays.

13. An improved imaging apparatus in accordance with claim 10, wherein the modulating frequency applied by said modulating means operates to amplitude modulate a beam intensity of each said electromagnetic ray is less than approximately one percent of the carrier frequency.

14. An improved imaging apparatus in accordance with claim 10, wherein said modulating means includes means for amplitude modulating a beam intensity of each said electromagnetic ray by a different modulation frequency.

15. An improved imaging apparatus in accordance with claim 1, wherein said applying means comprises sequencing means for sequentially applying said plurality of electromagnetic rays to the object.

16. In an apparatus for imaging attenuation and phase shift characteristics of an object including applying means for sequentially applying to a surface of the object a sequence of intensity modulated electromagnetic rays each having a carrier frequency in an optical frequency spectrum, and detecting means for detecting the electromagnetic rays after attenuation and phase shifting by each of a plurality of voxels (volume elements of interest), the improvement wherein said voxels are disposed in an array of n dimensions where n is at least equal to 1 and said detecting means comprises only a single optical detecting cell for detecting electromagnetic radiation resulting at a single point from attenuation and phase shift of each of said sequence of rays by said plurality of voxels, and processing means for processing an output signal from said single cell to provide data identifying optical attenuation and phase shift characteristics of each of said voxels thereby to image said plurality of voxels, wherein said applying means comprises modulating means for modulating each of said sequence of electromagnetic rays, thereby producing a sequence of intensity modulated electromagnetic rays, and for sequentially applying said sequence of modulated electromagnetic rays to said surface of said object.

17. In an apparatus for imaging optical attenuation and phase shift characteristics of an object including applying means for applying to a surface of the object a plurality of electromagnetic rays each having a carrier frequency in an optical frequency spectrum, each of said rays modulated by a modulation frequency, and detecting means for detecting the electromagnetic rays after attenuation and phase shifting by each of a plurality of voxels (volume elements of interest), the improvement wherein said voxels are disposed in an array of n dimensions where n is at least equal to 1 and said detecting means comprises only a single optical detecting cell for detecting electromagnetic radiation resulting at a single point from attenuation and phase shift of said plurality of rays by said plurality of voxels, and processing means for processing an output signal from said single cell to provide data identifying optical attenuation and phase shift characteristics of each of said voxels thereby to image said plurality of voxels.

* * * * *